(12) United States Patent
Gitman (10) Patent No.: US 9,717,521 B2
(45) Date of Patent: Aug. 1, 2017

(54) SURGICAL KNIFE AND TOOLS ADAPTED FOR SIMPLIFIED BLADE REMOVAL

(71) Applicant: ScalPal LLC, Wilmington, DE (US)

(72) Inventor: Eliot Robert Gitman, Jerusalem (IL)

(73) Assignee: ScalPal LLC, Wilmington, DE (US)

( * ) Notice: Subject to any disclaimer, the term of this patent is extended or adjusted under 35 U.S.C. 154(b) by 131 days.

(21) Appl. No.: 14/426,233

(22) PCT Filed: Jun. 10, 2013

(86) PCT No.: PCT/IL2013/050496
§ 371 (c)(1),
(2) Date: Mar. 5, 2015

(87) PCT Pub. No.: WO2014/037933
PCT Pub. Date: Mar. 13, 2014

(65) Prior Publication Data
US 2015/0250491 A1    Sep. 10, 2015

(30) Foreign Application Priority Data

Sep. 6, 2012 (IL) .......................................... 221825

(51) Int. Cl.
*A61B 17/3213* (2006.01)
*A61B 17/3217* (2006.01)
*A61B 17/3211* (2006.01)

(52) U.S. Cl.
CPC ...... *A61B 17/3217* (2013.01); *A61B 17/3213* (2013.01); *A61B 2017/32116* (2013.01)

(58) Field of Classification Search
CPC ............ A61B 17/3213; A61B 17/3217; A61B 17/3211; A61B 17/32113; A61B 2017/32116; Y10T 29/53683; Y10T 29/53943; Y10T 29/49815; Y10T 29/49822; Y10T 29/49824
USPC .................................. 30/340, 151; 606/167
See application file for complete search history.

(56) References Cited

U.S. PATENT DOCUMENTS

| 1,448,305 A | 3/1923 | Langbein |
| 2,257,141 A | 9/1941 | Waugh |
| 2,454,353 A | 11/1948 | Steele |
| 4,903,390 A * | 2/1990 | Vidal ................. A61B 17/3217 206/355 |

(Continued)

FOREIGN PATENT DOCUMENTS

| GB | 1596199 A | 5/1981 |
| GB | 2417453 A | 3/2006 |
| WO | 2010/000989 A1 | 1/2010 |

*Primary Examiner* — Phong Nguyen
(74) *Attorney, Agent, or Firm* — Kelly & Kelley, LLP (57) ABSTRACT

A knife (10) has a handle (15) with a mount (16) for affixing a removable blade (11). A concave surface (17) of the mount supports an elongate protrusion (18) for engaging a complementary slot (12) in the blade and reaches a landing (20) rearward of the tip that is exposed when the blade is mounted on the handle with a surface of the blade being completely supported by the concave surface. A channel (25) in the landing is dimensioned such that a rearmost part (26) thereof remains exposed when the blade is mounted on the handle. The blade is removed by inserting a curved lever (30) into the channel underneath a rearmost part of the blade and swiveling the lever so as to disengage the blade from the elongate protrusion.

9 Claims, 5 Drawing Sheets

(56) References Cited

U.S. PATENT DOCUMENTS

| | | | |
|---|---|---|---|
| 5,361,902 A * | 11/1994 | Abidin | A61B 17/3217 |
| | | | 206/354 |
| 5,875,532 A * | 3/1999 | Musgrave | A61B 17/3215 |
| | | | 206/355 |
| 5,875,533 A | 3/1999 | Henry | |
| 5,967,317 A * | 10/1999 | Wright | A61M 5/3205 |
| | | | 206/366 |
| D589,619 S | 3/2009 | Wu | |
| 2004/0111853 A1* | 6/2004 | Hoftman | A61B 17/3217 |
| | | | 29/239 |
| 2005/0065541 A1 | 3/2005 | Abidin et al. | |
| 2007/0039844 A1* | 2/2007 | Zyzelewski | A61B 50/362 |
| | | | 206/363 |
| 2010/0005630 A1 | 1/2010 | Gitman et al. | |

* cited by examiner

SURGICAL KNIFE AND TOOLS ADAPTED FOR SIMPLIFIED BLADE REMOVAL

FIELD OF THE INVENTION

This invention relates to surgical scalpels.

BACKGROUND OF THE INVENTION

A conventional surgical scalpel comprises a reusable handle having a tang at one end on which a replaceable slotted blade is mounted. The handle is intended to be used repeatedly, but the blade is normally discarded after each instance of use. Some operations may require several blades to be used successively on the same handle, e.g. where the blades become dull or contaminated, or a different style of blade is required at different stages of the operation.

Figures 1, 2:
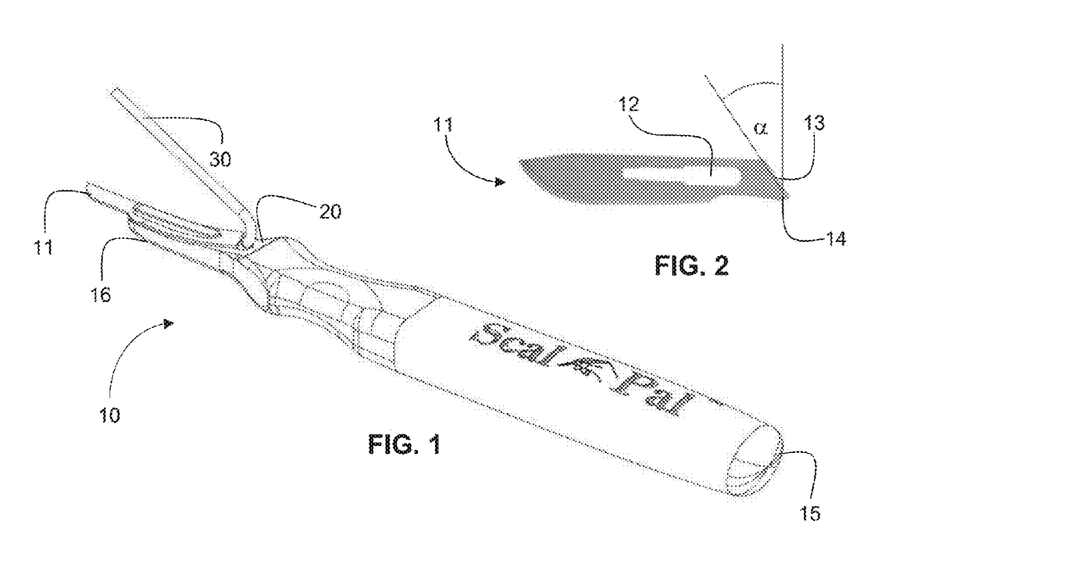
FIG. 1 is a pictorial representation showing a perspective view of a surgical knife according to an embodiment of the invention.
FIG. 2 is a pictorial representation showing a removable scalpel blade for use with the surgical knife shown in FIG. 1.

To remove the blade from the handle, the heel portion of the slotted blade shown in FIG. 1 must be bent out of its plane (i.e. transversely to the handle), and then moved axially along the tang so that the heel portion rides over the tang thereby releasing the tang from the slot. The slot is of keyhole shape, which as seen in the figure is wider at the rear than at the front so as to facilitate partial insertion of the tang into the wide front portion of the slot. The tang has a recessed protrusion dimensioned for securing the narrow sides of the slot. The length of keyhole slot is the same as the protrusion, so that when the blade is mounted on the protrusion and pushed backward, the narrow portion of the keyhole slot engages opposing recesses in the sides of the protrusion toward its front edge. The blade is then secured by sliding along the protrusion until a rear edge of the wide portion of the keyhole slot engages a rear edge of the protrusion. Manual removal of the blade requires that the rear edge of the keyhole slot be raised clear of the rear edge of the protrusion so as to allow the blade to be slid along the recesses in a reverse procedure. This can be difficult, particularly when the scalpel is wet. With the ever increasing spread of blood transmitted diseases, the removal is also a dangerous procedure as any accidental injury from the blade can have life-threatening ramifications.

Many devices have been developed in an effort to facilitate the removal of the blade from the scalpel, and to render the removal procedure less dangerous. Some require two-handed operation such as those described in GB 1 596 199, U.S. Pat. Nos. 244,094, 4,378,624, 730,376, 4,903,390, 5,088,173 and 5,163,553. Other devices require the user to bend, pivot or flex the scalpel handle to cause the blade to be dismounted such as those described in U.S. Pat. Nos. 1,648,408, 4,168,777, 4,270,416, 4,466,539, 4,736,844, 4,746,016 and 5,035,703.

U.S. Pat. No. 5,875,533 discloses a device for removing a blade from the tang of a scalpel. The scalpel is inserted in, and withdrawn from, the blade remover, which has a rocker block that pivots about an axis transverse to the insertion path. When the scalpel is inserted into the blade remover, its tang pushes against a contact surface of the rocker block, causing the rocker block to pivot. Legs at the other end of the rocker block apply a transverse force to the heel of the blade on either side of the tang, thereby lifting the heel of the blade off the tang and allowing its removal. The blade remover may be mounted in the lid of a sharps container.

What appears to characterize known devices is that a specialized removal tool is provided into which the scalpel is inserted. Upon insertion, the blade is retained within the tool allowing the tang to be removed. Tools that allow single-handed operation appear generally to be bulky and often to require anchoring in some way.

In order to allow conventional blade removal devices to make contact with the blade in order to provide the required purchase that allows such devices to operate it is usual for the blade to be wider than the tang. The resulting overhang on either side of the tang allows the blade to be gripped by the blade removal device, this of course being a prerequisite to its effective removal. However, it has been found that this is prone to a number of disadvantages. First, in use the blade is not supported by the tang over its entire surface and the narrower the tang the more pronounced this is, leading to unstable support of the blade.

Secondly, and independent of its width, in most known scalpels, the tang has a flat support surface for supporting parallel tracks that accommodate the narrow portion of keyhole slot in the blade. The tracks necessarily are slightly narrower than the width of the narrow portion of the keyhole slot, thus giving rise to a certain play which manifests itself as wobble. This is undesirable and militates against precise control of the blade, which is clearly a prerequisite for fine surgical procedures.

One exception to this construction of which we are aware is U.S. Design Pat. No. D 589,619 to Wu, which discloses a shaped disposable scalpel. The scalpel has a flat tang whose width is the same as the blade.

The blade is held flat against the tang apart from the rear edge of the blade, which is slightly lifted by the stepped portion of the tang and abuts a shaped recess in the handle. The stepped portion of the tang creates an air gap between the lower surface of the blade and the tang. This allows insertion of a thin flat object, which can then lift the rear portion of the blade off the tracked protrusion and allow the blade to be slid off the tracked protrusion in known manner. This appears to be the only way to remove the blade since there is no purchase at its rear edge owing to its abutting proximity with the shaped recess of the handle. Likewise, as noted above, there is no purchase at the sides of the blade owing to its width being the same as the tang.

U.S. Pat. No. 2,257,141 discloses a surgical knife comprising a handle having at one end a mount having a projection that supports a slot in a scalpel blade. The handle has an elongated groove that passes under the heel of the blade, thus facilitating its removal from the handle. Removal of the blade requires two simultaneous actions. First, the rear edge of the blade is grasped using forceps inserted into the groove. The blade is then flexed so that its heel is lifted from the projection and the blade is the grasped at its forward end and pulled off the mount.

U.S. Pat. Nos. 1,448,305 and 2,454,353 disclose arrangements for connecting and securing together a removable scalpel blade and a handle. The handle has a tang having a pin that engages an aperture in the blade, which is flexed so that a rear edge of the blade is frictionally supported by a rear landing of the handle.

U.S. Pat. No. 4,903,390 discloses a scalpel blade removal and storage apparatus having a disposable plastic housing having an internal channel for receiving the blade and positively locates the tang portion of the handle within the housing. The blade stripping mechanism comprises an integrally formed, spring loaded lever arm disposed externally of the housing. Pressing the lever deflects the heel of the blade away from the tang and over into a recessed stop or pocket formed near the forward portion of the housing. Retraction of the handle strips the blade from the handle.

GB 1 596 199 discloses an apparatus for removing the blade from a scalpel handle wherein the blade is mounted on the scalpel handle via a grooved boss with a shoulder engaging a slot in the blade. The apparatus includes a body having an aperture to receive the blade end of the scalpel and abutment means adjacent the aperture to deform the blade to disengage it from the shoulder and hold the blade while the handle is withdrawn.

WO 2010/000989 discloses a blade removal device having two articulated jaws that are commonly hinged at their ends and whose opposite ends have scissor-type handles allowing the jaws to be operated between thumb and forefinger. A blade is inserted into the space between the jaws, which are then closed so as to grip the blade and allow its removal from its handle by a lateral pulling movement.

GB 2 417 453 discloses a blade removal device for a scalpel having two hingedly connected components defining opposing shaped recesses for accommodating a scalpel blade, which retained inside the device when the scalpel handle is withdrawn.

There is clearly a need for a scalpel whose handle may be non-disposable but to which disposable scalpel blades can be removably attached in such a manner as to reduce the wobble that characterizes known designs.

SUMMARY OF THE INVENTION

The invention provides a modified scalpel that lends itself more easily to removal of the blade while significantly reducing the wobble that characterizes known designs.

In accordance with different aspects of the invention there is provided a knife handle and a blade removal tool adapted for receiving a removable blade having the features of the respective independent claims.

The knife includes a handle having a mount for affixing the blade. The mount has a concave surface supporting an elongate protrusion for engaging a complementary slot in the blade, the concave surface reaching a landing located sufficiently rearward of the tip so as to remain exposed when the blade is mounted on the handle with a surface of the blade being completely supported by said concave surface. The concave surface induces slight flexing of the blade, which creates tension that urges the front of the blade upward against the shoulder, thereby securing the blade on the handle.

A channel in the landing is dimensioned such that a rearmost part thereof remains exposed when the blade is mounted on the handle, thereby allowing the blade to be removed by inserting a curved lever into the channel underneath a rearmost part of the blade and swiveling the lever so as to lift a rear portion of the blade and facilitate its sliding removal from the elongate protrusion.

The blade removal tool may be adapted for use with the scalpel according to the invention or may be adapted for use with conventional scalpels. In either case, the removed blade is retained inside the receptacle which may be safely disposed of outside the operating theater, thus avoiding the current tendency to collect multiple used blades often from different patients in a central garbage dispenser, which is located in the operating theater and serves as a hive of bacteria prior to its eventual disposal.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

With reference to FIGS. 1 to 8, there is shown a surgical scalpel 10 adapted for receiving a removable blade 11 having an elongate keyhole slot 12. A rear edge 13 of the blade is inclined at an acute angle α the vertical, thus creating a corner 14 on the same side as the cutting edge of the blade. The knife comprises a handle 15 having a mount 16 for affixing the blade and having a concave surface 17 supporting an elongate protrusion 18 that is complementary to the slot 12 in the blade, which it engages when the blade 11 is mounted on the handle 15. The mount 16 corresponds to the tang as discussed in the prior art. However, whereas in conventional tools, the tang is narrower than the blade such that part of the blade overhangs the tang and provides purchase for easy removal of the blade, the mount 16 is dimensioned for supporting the blade 11 with no overhang. On the one hand, this provides better and more stable support, but on the other hand requires a different approach for removal of the blade in cases where the scalpel is intended for use with interchangeable blades. The elongate protrusion 18 is recessed for sliding accommodation of the narrow portion of the keyhole slot 12. These features are not described in further detail since they are known per se and have been described in detail above with reference to FIG. 1.

Figure 3:
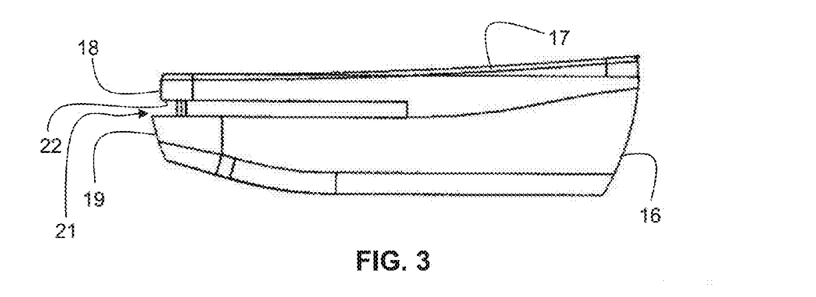
FIGS. 3 to 7 are enlarged details of the surgical knife shown in FIG. 1.
Figure 4A:
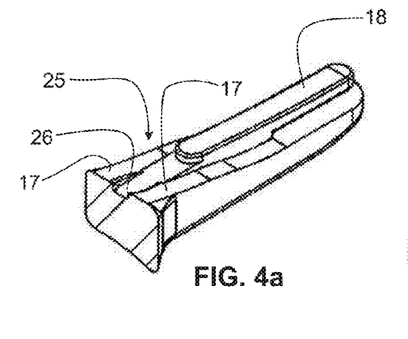
Figure 4B:
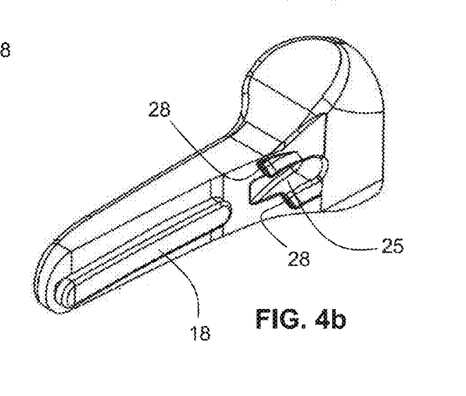
Figure 5:
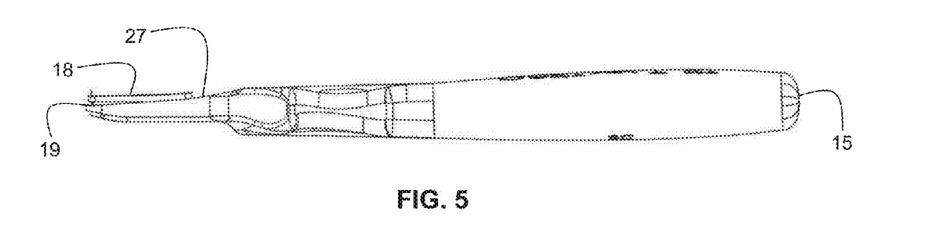
Figure 6:
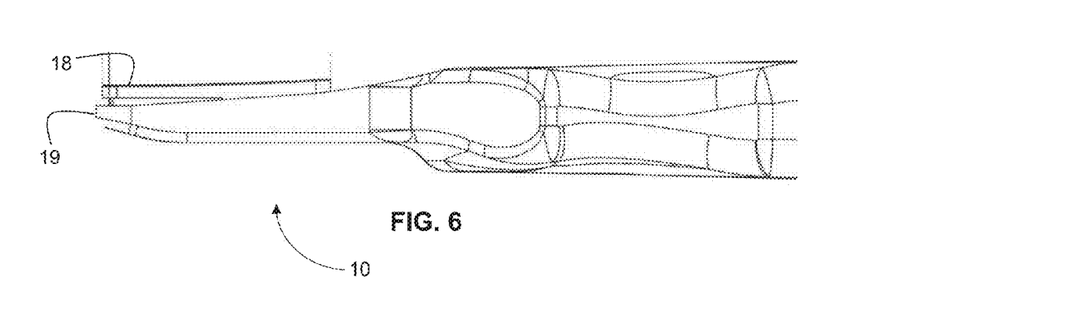
Figure 7:
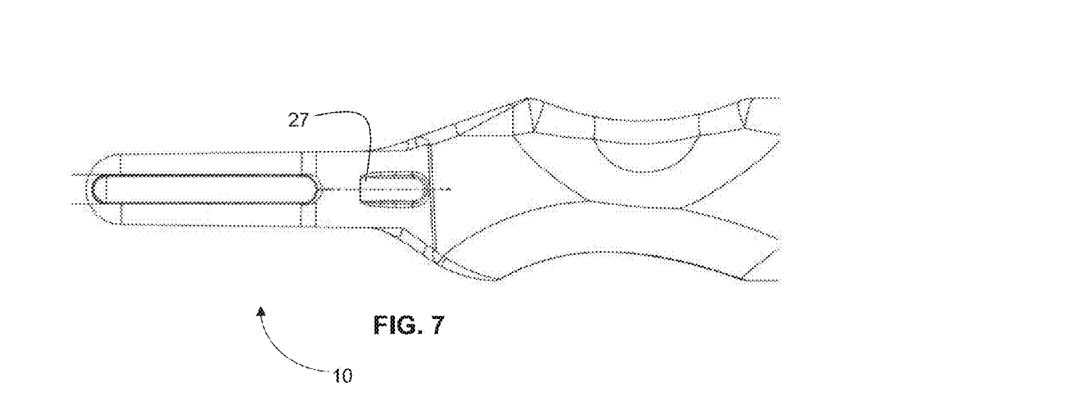
Figure 8:
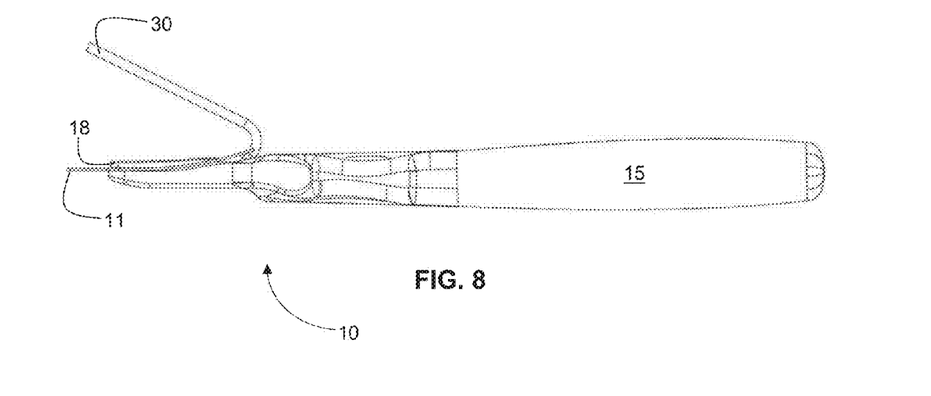
FIG. 8 is a pictorial representation showing a side elevation of the surgical knife shown in FIG. 1 during but prior to removal of the blade.

The upper surface at a tip 19 of the handle is generally flat and abuts the concave surface 17, which extends to an elevated landing 20 that is located sufficiently to the rear of the tip so as to remain exposed when the blade is mounted on the handle. As best seen in FIG. 3, a front end of the mount is cut away to form a recess 21 so that an upper surface of the protrusion 18 forms a shoulder 22 that overhangs the recess 21. The blade 11 is mounted on the handle 15 by aligning the slot 12 of the blade 11 with the protrusion 18 and pushing the blade backward until a front edge of the slot 12 is engaged within the recess 21. The concave surface 17 fully supports the blade 11 over its entire surface while inducing slight flexing of the blade 11, which creates tension that urges the front of the blade upward against the shoulder 22, thereby securing the blade 11 on the handle. An elongate channel 25 (shown in FIGS. 4a and 4b) is formed in the elevated landing 20 extending forward toward the tip 19 and being dimensioned such that a rearmost part 26 thereof remains exposed when the blade is mounted on the handle. A remaining part 27 of the channel 25 lies under a rear part of the blade when the blade is mounted on the handle. Preferably, a lower front surface of the handle 15 near the tip 19 is chamfered so as to provide a convenient platform for resting on the surgeon's middle finger during use and allowing finer control of the scalpel. As shown in FIG. 4b, the elevated landing 20 may be provided with a ridge 28 that abuts the rear edge of the blade 11 when attached. The ridge 28 is angled according to the angle α of the rear edge of the blade 11 as shown in FIG. 2 so as to provide a snug fit that serves to provide additional support and stability. The ridge 28 intersects the channel 25 so that the rear of the channel remains accessible from the ridge and allows a tool to be inserted into the channel 25 for removing the blade.

Figure 15A:
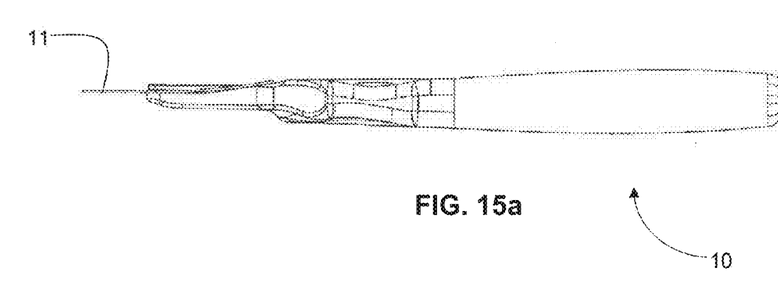
FIGS. 15a and 15b are pictorial representations showing removal of the blade using conventional forceps.
Figure 15B:
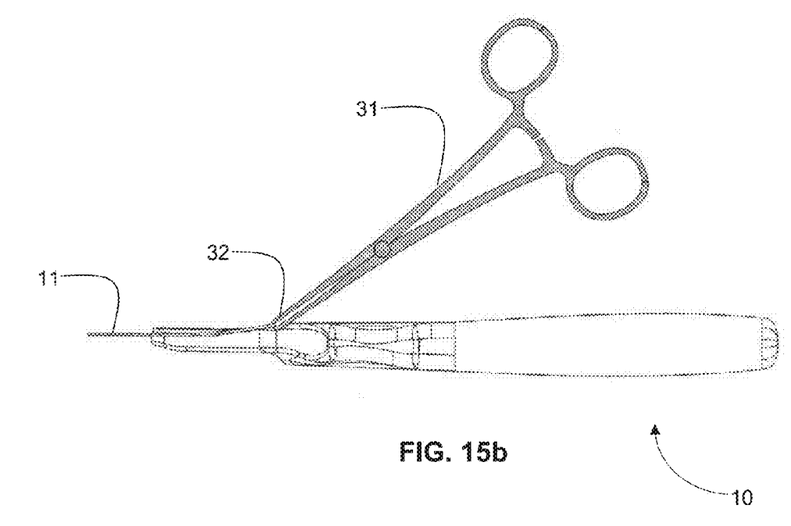

The blade 11 is removed by inserting a hook or curved lever 30 into the channel 25 underneath a rearmost part of the blade and swiveling the lever so as to disengage the blade from the elongate protrusion. Alternatively, as shown in FIGS. 15 and 15b the working tip of a standard forceps 31 or tweezers or any other similar instrument having a pair of opposing jaws 32 may be inserted into the channel 25 in order to grip the rear portion of the blade between the jaws. Owing to the elevation of the landing 20, the lower jaw of the instrument points downward, such that closing the jaws while tilting the instrument upwardly on the elevated landing lifts the rear portion of the blade off the tang whereby slight forward movement of the instrument removes the blade while retaining it between the two jaws of the instrument. In such an approach, the blade is removed away from the body of the user thus rendering it completely safe and allowing easy disposal of the blade. In this embodiment, the channel 25 serves only to allow the tip of the removal tool to grasp the rear edge of the blade. To this end, the channel need not be elongated but can be a recess or depression that is accessible from the rear edge of the blade and is dimensioned to accommodate the tip of a removal tool.

Figure 9:
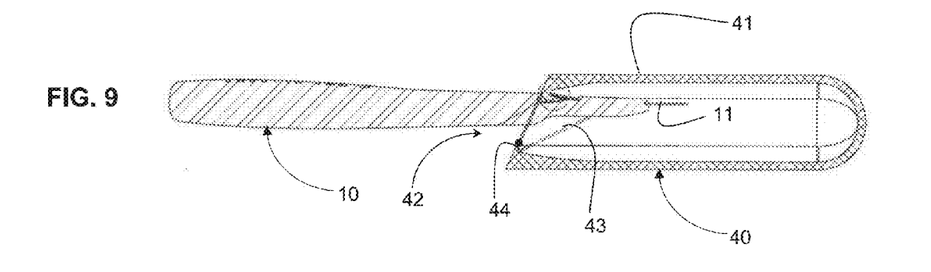
FIGS. 9 and 10 are pictorial representations showing details of a blade removal tool according to a first embodiment for removing a blade from a surgical scalpel modified according to FIGS. 1 to 8.
Figure 10:
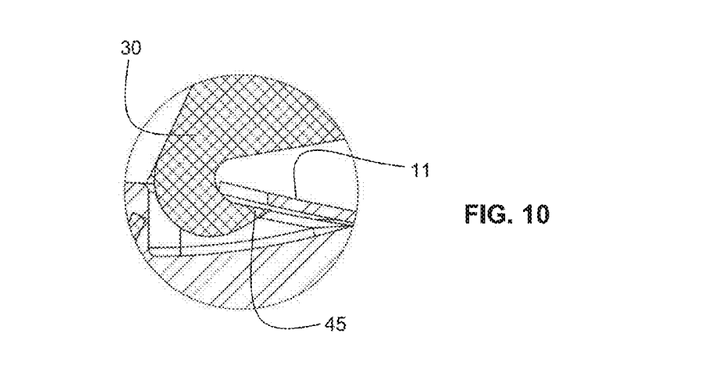

In some embodiments such as shown in FIGS. 9 and 10, the curved lever 30 may be pivotably mounted toward the open end of an otherwise closed receptacle dimensioned for accommodating the blade into which the scalpel blade is inserted, so that when the end of the lever 30 is hooked underneath the rear part of the blade and pivoted, the blade is removed and is collected into the receptacle. The receptacle and the blade thus collected may then be safely disposed of.

FIGS. 9 and 10 are pictorial representations showing details of a blade removal tool 40 according to a first embodiment for removing a blade from the surgical scalpel 10 having an elongate channel 25 as described above with reference to FIGS. 1 to 8. The blade removal tool 40 comprises a generally closed receptacle 41 having an opening 42 to which a resilient shutter 43 is hinged at a lower edge for pivotally opening about a hinge axis shown as 44. An upper edge of the opening 42 curves inwardly, having a claw 45 that points inside the receptacle 41 towards its closed end and is dimensioned such that it is accommodated within the elongate channel 25.

Upon insertion of the scalpel 10 into the opening 42 of the blade removal tool 40, the shutter 43 is resiliently pushed inward. The scalpel 10 is inserted until the channel 25 becomes aligned with the claw 45, whereupon lifting the scalpel upward at its front tip urges the channel 25 into upward engagement with the claw 45 behind the rear edge of the blade 11. This is shown in FIG. 9 and in enlarged detail in FIG. 10. Withdrawing the scalpel 10 from the blade removal tool 40 now lifts the rear edge of the blade 11, thereby removing it from the protrusion 18 whereupon it falls into the receptacle 41. Upon complete removal of the scalpel 10 from the blade removal tool 40, the blade 11 remains inside the receptacle 41 and the shutter 43 is closed under its resilient bias thereby retaining the removed blade inside the receptacle 41 and preventing its unintentional dislodgement. The receptacle may be formed of transparent material so as to provide an indication as to one or more blades have been removed from the scalpel without the need to peer inside the receptacle. The complete assembly comprising the blade removal tool 40 and any blades 11 contained therein may be safely disposed of outside the operating theater. The small size and cost of the blade removal tool 40 make it unnecessary to collect multiple used blades from more than one patient in a central garbage dispenser, which is located in the operating theater and serves as a hive of bacteria prior to its eventual disposal.

Figure 11:
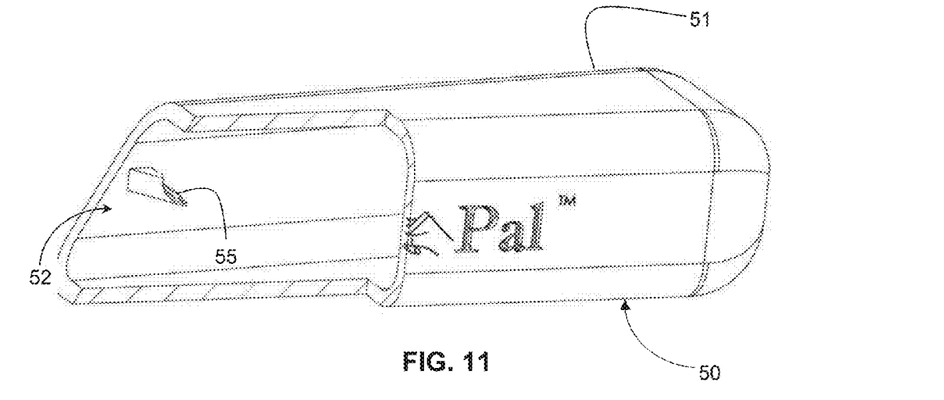
FIGS. 11 to 14 are pictorial representations showing details of a blade removal tool according to a second embodiment for removing a blade from a conventional surgical scalpel.
Figure 12:
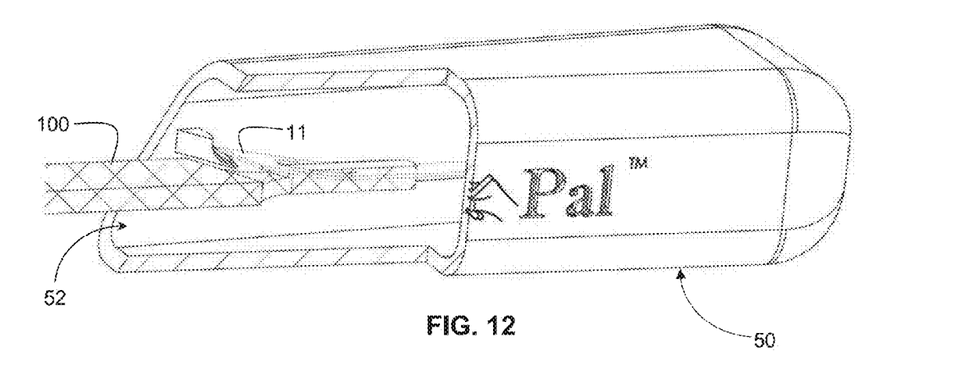
Figure 13:
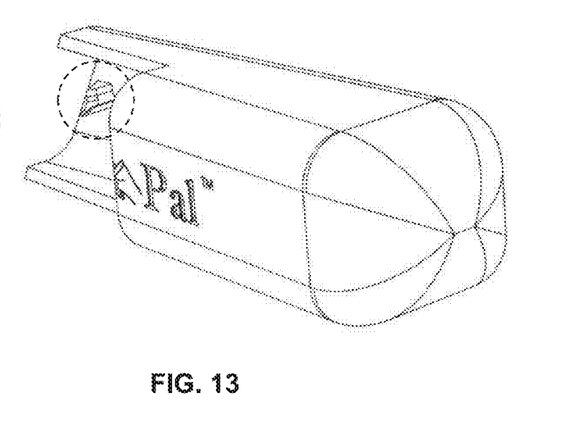
Figure 14:
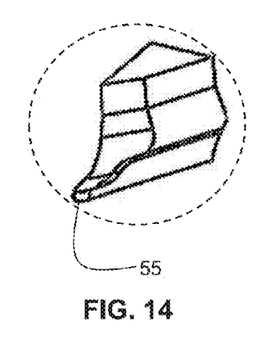

The blade removal tool 40 shown in FIGS. 10 and 11 is customized for use with the scalpel 10 shown in FIGS. 1 to 8, where the mount 16 is dimensioned for supporting the blade 11 with no overhang.

FIGS. 11 to 14 are pictorial representations showing details of a blade removal tool 50 according to a second embodiment for removing a blade from a conventional surgical scalpel shown as 100 as described in the background. The blade removal tool 50 comprises a generally closed receptacle 51 having an opening 52 to which a resilient shutter (not shown) is hinged at a lower edge. Attached to an inner side surface of the receptacle 51 is a claw 55 that is shown enlarged in FIG. 14 where it is seen that the claw 55 is directed laterally from the inner wall of the receptacle 51 supporting the claw to the opposite wall.

In use, the scalpel 100 is inserted into the opening 52 of the blade removal tool 50 below the claw 55, whereby the shutter is resiliently pushed inward. As noted above with reference to FIG. 2, the rear edge 13 of the blade is inclined at an acute angle α the vertical, thus creating a corner 14 that overhangs the mount. The scalpel is inserted until the corner 14 engages the outwardly protruding claw 55 and the scalpel is then shifted laterally toward the claw while pulling downward, whereby the claw engages more of the overhanging edge of the blade and lifts it off from the mount. The scalpel 10 is now removed from the blade removal tool 50 whereby the blade 11 falls into the receptacle 51. Upon complete removal of the scalpel 10 from the blade removal tool 50, the blade 11 remains inside the receptacle 51 and the shutter is closed under its resilient bias thereby retaining the removed blade inside the receptacle 51 and preventing its unintentional dislodgement. The receptacle may be formed of transparent material so as to provide an indication as to one or more blades have been removed from the scalpel without the need to peer inside the receptacle.

It will be appreciated that while the invention has been described with particular reference to a surgical scalpel, the principles of the invention are equally applicable for any knife having a removable or replaceable blade that fits on to a handle in a similar manner.

It should be noted that since the blade 11 is fully supported on the mount 16 in the scalpel 10 according to the invention without any overhang and, moreover, since the blade is removed by inserting a hook into a channel or hollow formed in the mount under the rear edge 13 of the blade, the shape of the rear edge of the blade has no bearing on the design of the scalpel. The blade 11 shown and described with reference to FIG. 2 has an inclined rear edge 13. But this is not essential to proper operation of the scalpel, which is equally effective even if the rear edge of the blade is not inclined as shown.

Likewise, the blade removal tool 40 shown in FIGS. 9 and 10 being adapted for use with such a scalpel operates independent of the shape of the rear edge of the blade. On the other hand, the blade removal tool 50 shown in FIGS. 11 to 14 is adapted to engage an edge of the blade that protrudes beyond the side edges of the mount. In this case, the inclined rear edge 13 of the blade, while again not mandatory, offers an advantage in that it presents a sharp corner 14 that is more easily engaged by the claw 55 as explained above.

It should also be noted that if desired the blade removal tool according to either embodiment may be provided with means for attaching to a fixed structure so as to allow one-handed operation.

Finally it is noted that the description relates to two complementary approaches to removing the blade: either by levering the blade off its tang using a lever, which may optionally be located inside a receptacle; or using a two-jawed instrument that allows the blade to be removed and then disposed of safely without the need to touch the blade. However, while the invention provides a mechanism for removing the blade without the need to touch it, it is to be understood that a user may decide to lever the blade off its tang and dispose of it in a manner that may not be surgically safe. Obviously, other than the risk of accidental cuts, there is no inherent medical risk in removing a disposable blade from a craft knife. So it is clear that in its broadest aspect the invention provides an improved structure for attaching a blade to a knife that allows for simplified removal using a lever.

The invention claimed is:

1. A blade removal tool for removing a blade from a knife handle having an elongate channel or a recess in a mount of the handle disposed toward a rear of the mount, said elongate channel or recess extending along the mount so that when a surface of the blade is supported on the mount, the elongate channel or recess lies at least partially underneath a rear edge of the blade and has a rearmost part that remains accessible thereby forming a cavity in the mount underneath the surface of the blade at the rear edge thereof, said blade removal tool comprising:
   a generally closed receptacle having an opening, and
   a claw supported within the receptacle and pointing inside the receptacle towards a closed end thereof, the claw being dimensioned for accommodation within the cavity at the rearmost part of the elongate channel or recess of the knife with a tip of the claw engaging said surface of the blade;
   whereby withdrawing the knife toward the opening away from the claw removes the blade and retains the blade inside the receptacle.

2. The blade removal tool according to claim 1, wherein:
   the receptacle has an opening supporting a resilient shutter at an edge of the opening for pivotally opening about a hinge axis and being adapted to resiliently close when the knife is removed from the receptacle.

3. The blade removal tool according to claim 2, wherein the claw is mounted at an edge of the opening opposite the edge supporting the resilient shutter.

4. The blade removal tool according to claim 1, wherein the claw is mounted at an edge of the opening.

5. The blade removal tool according to claim 1, wherein the receptacle is formed of transparent material so as to provide an indication as to one or more blades have been removed from the scalpel.

6. A blade removal system, comprising a knife having a removable blade and a blade removal tool;
   the knife comprising:
   a handle having an elongate channel or a recess in a mount of the handle disposed toward a rear edge of the blade, said elongate channel or recess extending along the mount so that when a surface of the blade is supported on the mount, the elongate channel or recess lies at least partially underneath a rear edge of the blade and has a rearmost part that remains accessible thereby forming a cavity in the mount underneath the surface of the blade at the rear edge thereof; and
   the blade removal tool comprising:
   a generally closed receptacle having an opening,
   a claw supported within and pointing inside the receptacle towards a closed end thereof, the claw being dimensioned for accommodation within the cavity at the rearmost part of the elongate channel or recess of the knife with a tip of the claw engaging said surface of the blade and removing the blade when the knife is withdrawn from the receptacle and retaining the blade inside the receptacle.

7. The blade removal system according to claim 6, wherein the receptacle has an opening supporting a resilient shutter at an edge of the opening for pivotally opening about a hinge axis.

8. The blade removal system according to any one of claims 6, wherein the claw is mounted at an edge of the opening of the receptacle.

9. The blade removal tool according to claim 6, wherein the receptacle is formed of transparent material so as to provide an indication as to one or more blades have been removed from the scalpel.

* * * * *